United States Patent
Edmond

(10) Patent No.: US 8,906,066 B2
(45) Date of Patent: Dec. 9, 2014

(54) NON-PEDICLE BASED INTERSPINOUS SPACER METHODS

(71) Applicant: US Spine, Inc., Salt Lake City, UT (US)

(72) Inventor: Elizabeth Watson Edmond, Ann Arbor, MI (US)

(73) Assignee: US Spine, Inc., Salt Lake City, UT (US)

( * ) Notice: Subject to any disclaimer, the term of this patent is extended or adjusted under 35 U.S.C. 154(b) by 0 days.

(21) Appl. No.: 13/751,941

(22) Filed: Jan. 28, 2013

(65) Prior Publication Data

US 2013/0261669 A1 Oct. 3, 2013

Related U.S. Application Data

(63) Continuation of application No. 11/690,884, filed on Mar. 26, 2007, now Pat. No. 8,361,116.

(60) Provisional application No. 60/785,617, filed on Mar. 24, 2006.

(51) Int. Cl.
*A61B 17/70* (2006.01)

(52) U.S. Cl.
CPC .......... *A61B 17/7068* (2013.01); *A61B 17/7065* (2013.01)
USPC ........................................ 606/249

(58) Field of Classification Search
USPC ............. 606/247–249, 279; 623/17.11–17.16
See application file for complete search history.

(56) References Cited

U.S. PATENT DOCUMENTS

| | | | |
|---|---|---|---|
| 5,496,318 A | 3/1996 | Howland et al. | |
| 5,885,284 A | 3/1999 | Errico et al. | |
| 6,126,660 A | 10/2000 | Dietz | |
| 6,440,169 B1 | 8/2002 | Elberg et al. | |
| 6,770,096 B2 | 8/2004 | Bolger et al. | |
| 6,949,123 B2 | 9/2005 | Reiley | |
| 7,238,204 B2 | 7/2007 | Le Couedic et al. | |
| 7,458,981 B2 | 12/2008 | Fielding et al. | |
| 7,476,251 B2 | 1/2009 | Zucherman et al. | |
| 7,520,887 B2 | 4/2009 | Maxy et al. | |
| 7,520,888 B2 | 4/2009 | Trieu | |
| 7,524,324 B2 | 4/2009 | Winslow et al. | |
| 7,585,313 B2 | 9/2009 | Kwak et al. | |
| 7,585,316 B2 | 9/2009 | Trieu | |
| 7,594,932 B2 | 9/2009 | Aferzon et al. | |
| 7,608,106 B2 | 10/2009 | Reiley | |
| 7,763,073 B2 | 7/2010 | Hawkins et al. | |
| 7,771,432 B2 | 8/2010 | Schwab et al. | |
| 7,776,091 B2 | 8/2010 | Mastrorio et al. | |
| 7,955,392 B2 | 6/2011 | Dewey et al. | |
| 8,007,517 B2 | 8/2011 | Lins et al. | |
| 8,075,593 B2 | 12/2011 | Hess | |
| 8,357,181 B2 | 1/2013 | Lange et al. | |
| 2005/0075643 A1* | 4/2005 | Schwab et al. | 606/90 |
| 2005/0203512 A1 | 9/2005 | Hawkins et al. | |
| 2005/0261768 A1* | 11/2005 | Trieu | 623/17.11 |

(Continued)

*Primary Examiner* — Matthew Lawson

(74) *Attorney, Agent, or Firm* — Phillips Ryther & Winchester; Matthew D. Thayne

(57) ABSTRACT

Methods for non-pedicle spinal fixation. In some implementations, at least one plate member may be placed between an upper spinous process and a lower spinous process of a spine. At least one scissoring element coupled to the at least one plate member may then be positioned to contact opposing lateral surfaces of the upper spinous process and to contact opposing lateral surfaces of the lower spinous process. The at least one scissoring element may then be locked into place to stabilize the spinous processes.

17 Claims, 2 Drawing Sheets

(56) References Cited

U.S. PATENT DOCUMENTS

| | | |
|---|---|---|
| 2006/0004447 A1 | 1/2006 | Mastrorio et al. |
| 2006/0089654 A1 | 4/2006 | Lins et al. |
| 2006/0293662 A1 * | 12/2006 | Boyer et al. ............ 606/61 |
| 2007/0100340 A1 | 5/2007 | Lange et al. |
| 2007/0161992 A1 | 7/2007 | Kwak et al. |
| 2008/0161818 A1 | 7/2008 | Kloss et al. |
| 2008/0167655 A1 | 7/2008 | Wang et al. |

\* cited by examiner

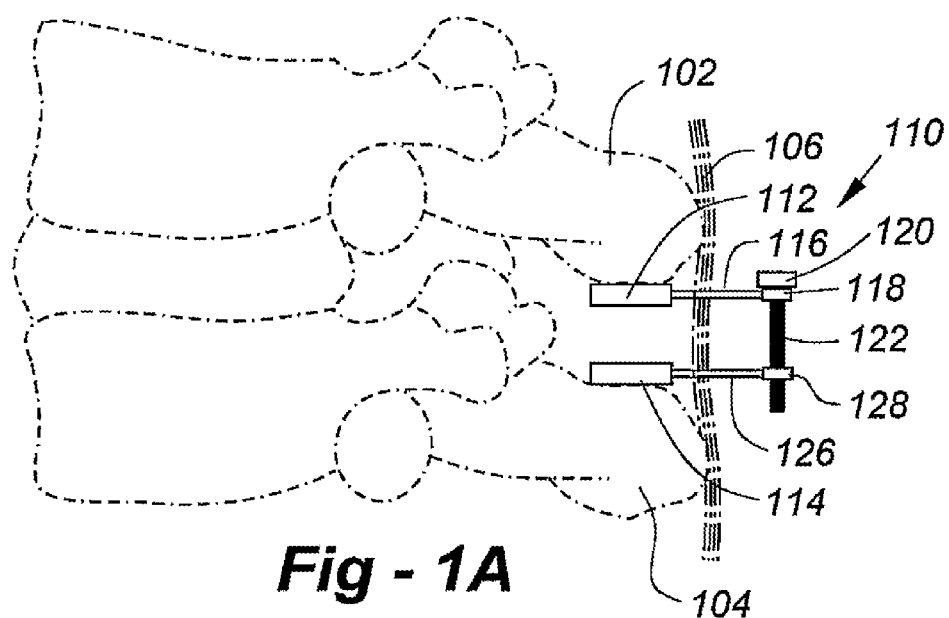
Fig - 1A
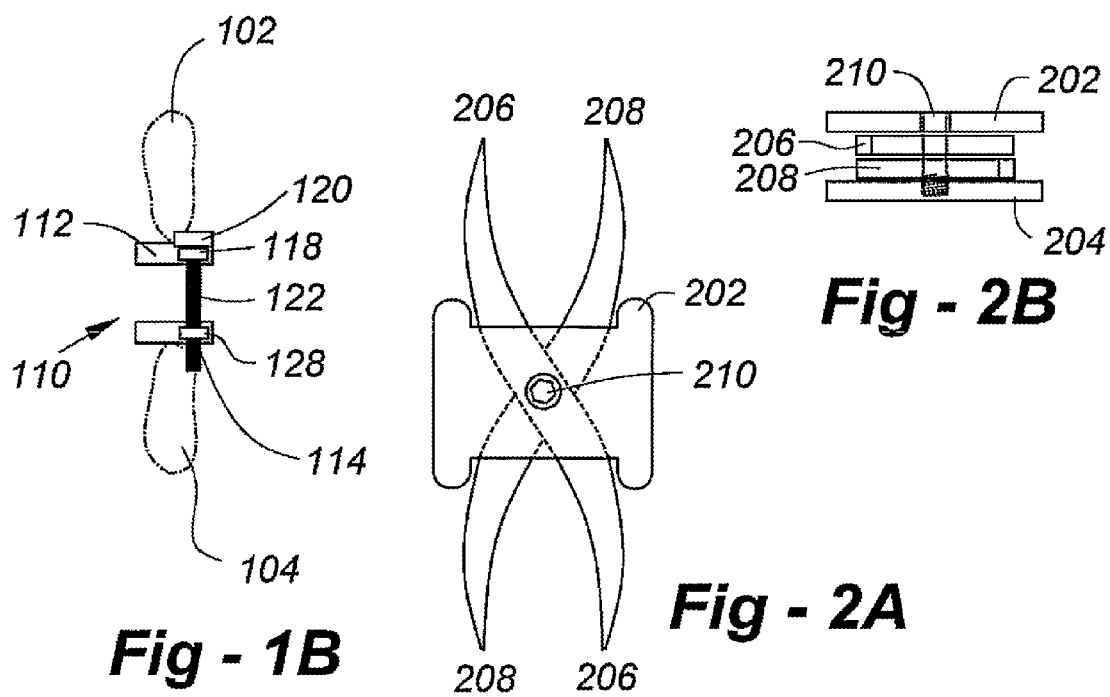
Fig - 1B
Fig - 2A
Fig - 2B

NON-PEDICLE BASED INTERSPINOUS SPACER METHODS

RELATED APPLICATIONS

This application is a continuation of patent application Ser. No. 11/690,884, filed on Mar. 26, 2007 and titled "Non-Pedicle Based Interspinous Spacer," which application claims the benefit under 35 U.S.C. §119(e) of U.S. Provisional Patent Application Ser. No. 60/785,617, filed on Mar. 24, 2006. The entire contents of both of the foregoing applications are incorporated herein by reference.

FIELD OF THE INVENTION

This invention relates generally to spinal stabilization devices and, in particular, to non-pedicle-based interspinous spacers.

BACKGROUND OF THE INVENTION

Natural intervertebral discs serve multiple purposes. First, they preserve correct anatomical spacing between adjacent vertebral bodies, allowing branching nerve bundles to function normally, without pain. Discs also facilitate natural flexion, extension, and lateral bending in support of daily physical activities. Discs further serve as "shock absorbers" for spinal loading.

However, for many reasons, natural discs can lose functionality, often leading to back pain. These sources may include physical trauma, degenerative disc disease, and other maladies. Today there are many options to stabilize spinal segments which may exhibit a loss of functionality. One option is spinal fusion, wherein a complete or partial discectomy is performed, with one or more cages or other mechanical devices being inserted into the disc space. Another option gaining in popularity is the use of "artificial discs," which typically include either a resilient central portion or mechanical elements that facilitate a certain degree of articulation.

Various types of intervertebral spacers are also available as valuable tools to promote spinal stabilization. Such devices may be used in conjunction with fusion, for example, to relieve pressure from the central vertebral column. Spacers may also be valuable in relieving spinal stenosis and other conditions resulting in back pain.

SUMMARY OF THE INVENTION

This invention resides in spinal distraction apparatus including at least one plate member having upper and lower surfaces adapted for placement between opposing upper and lower spinous processes having outer lateral surfaces. A pair of scissoring elements are hingedly affixed to the plate member. Each scissoring element has an end that extends beyond the upper surface of the plate member and an end that extends beyond the lower surface of the plate member, resulting in a pair of upwardly oriented scissoring elements with inner surfaces adapted for contact with the outer lateral surfaces of the upper spinous process and a pair of downwardly oriented scissoring elements with inner surfaces adapted for contact with the outer lateral surfaces of the lower spinous process. A device is provided for locking the scissoring elements in position once a desired degree of contact is made with the lateral surfaces.

In the preferred embodiment, the scissoring elements are sandwiched between a pair of opposing plate members, each having upper and lower surfaces adapted for placement between opposing upper and lower spinous processes, and the inner surfaces of the scissoring elements are concave. The device for locking the scissoring elements in position is a fastener that extends through a central portion of both scissoring elements and the plate members.

The apparatus may further include a retractor with upper and lower plates for spreading the upper and lower spinous processes apart to receive the plate with scissoring element(s), and wherein the upper and lower surfaces of the plate member have notches to accommodate the upper and lower plates.

BRIEF DESCRIPTION OF THE DRAWINGS

FIG. 1A is a lateral view of distraction apparatus according to the invention;

FIG. 1B is a posterior view of the distraction apparatus of FIG. 1A;

FIG. 2A is a drawing of a spinous process stabilization system according to the invention;

FIG. 2B is an end view of the system of FIG. 2A;

DETAILED DESCRIPTION OF THE PREFERRED EMBODIMENTS

Figure 3:
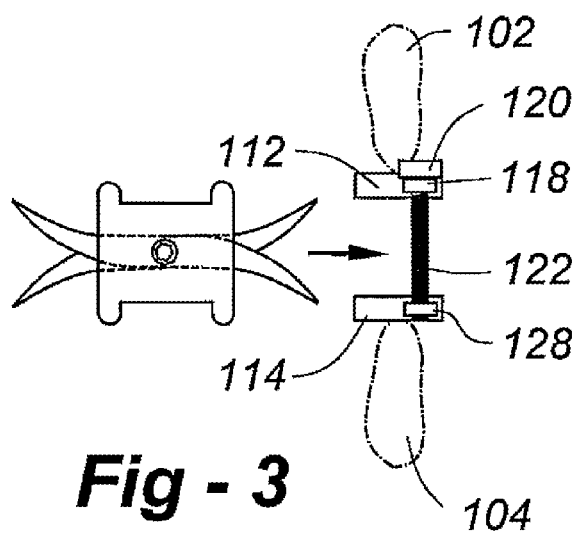
FIG. 3 is a drawing which shows a posterior view of spinous processes being distracted, and with the stabilization apparatus of FIGS. 2A and 2B being inserted.

Turning now to the drawings, FIG. 1A is a side view drawing which shows distraction apparatus according to the invention, indicated generally at 110. Such apparatus includes superior and inferior plates 112, 114, which are linked via members 116, 126 to elements 118, 128. Element 118 is a collar, which facilitates location, whereas element 128 is a threaded member which changes the relative position between plates 112, 114 in response to rotational force applied to head member 120. Rotation of head member 120 in one direction causes the distraction of spinous processes 102, 104, whereas rotation in the opposition direction allows the spinous processes to move toward one another. The supra spinous ligament is indicated at 106.

FIG. 1B is a posterior view of the system of FIG. 1A. The distraction mechanism proper, including collars 118, 128 and threaded element 122, are shown off to one side, though any appropriate placement facilitating distraction is acceptable. Indeed, distraction apparatus other than that just described are applicable to the invention, so long as the spacer described hereinbelow, may be accommodated.

Turning now to FIGS. 2A and 2B, these show a frontal view of an interspinous process spacer according to the invention, along with a side view (FIG. 2B). The spacer includes a plurality of opposing plates 202, 204, sandwiched therebetween are a pair of scissoring elements 206, 208. A threaded fastener used for tightening is indicated at 210.

Figure 4:
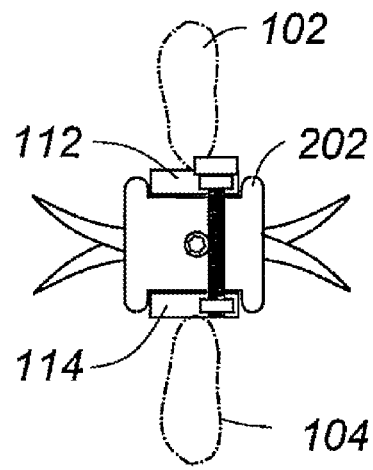
FIG. 4 shows the stabilization apparatus inserted, with the distraction mechanism still in place.

FIG. 3 shows the vertebral bodies being distracted through the operation of distraction system 110, moving the spinous processes 102, 104 apart from one another. This is carried out to an extent that allows the spacer system to be inserted, with the upper and lower surfaces of the spacer system cooperating with the opposing surfaces of the plates 112, 114, as shown in FIG. 4. Again, although the spacer system is shown and described in cooperation with an inventive distraction system 110, the invention is not limited in this regard, in that the spacer may be used in conjunction with any appropriate distraction system, so long as the spacer is inventively accommodated.

Figure 5:
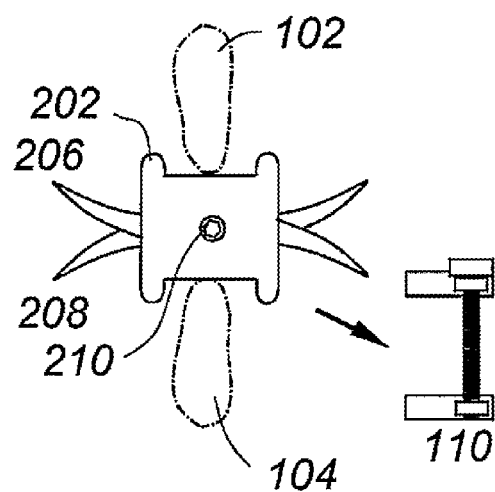
FIG. 5 is a drawing which shows the distraction apparatus being removed.
Figure 6:
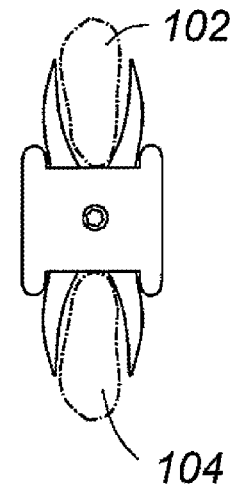
FIG. 6 is a posterior view showing the way in which scissoring elements are locked into place along upper and lower spinous processes to achieve stabilization according to the invention.

In FIG. 5, the distraction system 110 has been removed, allowing spinous processes 102, 104, to rest against the superior and inferior surfaces of the spacer as shown. Next, as shown in FIG. 6, the scissoring elements 206, 208, are rotated upwardly, as shown, thereby stabilizing the superior and inferior spinous processes 102, 104. At this time, the fastener 210 is tightened, locking the mechanism in place, providing a posterior column stabilization system that does not require pedicle implantation.

The invention claimed is:

1. A method for stabilizing a spine, comprising the steps of:
   placing at least one plate member between an upper spinous process and a lower spinous process of a spine; and
   rotating at least one scissoring element coupled to the at least one plate member such that an upper end of the at least one scissoring element is initially positioned below an upper surface of the at least one plate member and, after rotating, the upper end of the at least one scissoring element extends beyond the upper surface of the at least one plate member, such that at least a portion of the at least one scissoring element contacts a first outer lateral surface of the upper spinous process, such that at least a portion of the at least one scissoring element contacts a second outer lateral surface of the upper spinous process opposite from the first outer lateral surface of the upper spinous process, such that at least a portion of the at least one scissoring element contacts a first outer lateral surface of the lower spinous process, and such that at least a portion of the at least one scissoring element contacts a second outer lateral surface of the lower spinous process opposite from the first outer lateral surface of the lower spinous process, wherein the at least one plate member comprises a first plate member and a second plate member, and wherein the step of placing at least one plate member between an upper spinous process and a lower spinous process of a spine comprises placing the first plate member so as to abut the upper spinous process and placing the second plate member so as to abut the lower spinous process.

2. The method of claim 1, wherein the at least one scissoring element comprises at least two scissoring elements.

3. The method of claim 2, wherein the step of rotating at least one scissoring element comprises rotating the at least two scissoring elements such that at least a portion of a first scissoring element of the at least two scissoring elements contacts a portion of a lateral surface of the upper spinous process and such that at least a portion of a second scissoring element of the at least two scissoring elements contacts a portion of a second lateral surface of the upper spinous process opposite from the lateral surface.

4. The method of claim 3, wherein the at least two scissoring elements comprises a pair of scissoring elements, and wherein the step of rotating the at least two scissoring elements comprises:
   rotating the first scissoring element such that an upper end of the first scissoring element rotates to extend beyond an upper surface of the first plate member and a lower end of the first scissoring element rotates to extend beyond a lower surface of the second plate member; and
   rotating the second scissoring element such that an upper end of the second scissoring element rotates to extend beyond the upper surface of the first plate member and a lower end of the second scissoring element rotates to extend beyond the lower surface of the second plate member.

5. The method of claim 4, wherein the step of rotating the at least two scissoring elements comprises rotating the scissoring elements such that inner surfaces of the upper ends of the scissoring elements rotate into contact with opposing outer lateral surfaces of the upper spinous process and inner surfaces of the lower ends of the scissoring elements rotate into contact with opposing outer lateral surfaces of the lower spinous process.

6. The method of claim 5, wherein the step of rotating the at least two scissoring elements is performed so as to avoid extending the scissoring elements into the upper and lower spinous processes.

7. The method of claim 1, wherein the step of rotating at least one scissoring element is performed so as to avoid extending the at least one scissoring element into the upper and lower spinous processes.

8. The method of claim 1, wherein the at least one scissoring element comprises a pair of scissoring elements, and wherein inner surfaces of upper and lower ends of the scissoring elements are concave.

9. The method of claim 1, further comprising locking the at least one scissoring element to secure the at least one scissoring element in a fixed position to stabilize the upper and lower spinous processes.

10. The method of claim 1, wherein the step of placing at least one plate member between an upper spinous process and a lower spinous process of a spine comprises placing the first plate member such that an upper surface of the first plate member abuts a lower surface of the upper spinous process and a lower surface of the second plate member abuts an upper surface of the lower spinous process.

11. A method for stabilizing a spine, comprising the steps of:
    placing at least one plate member between an upper spinous process and a lower spinous process of a spine, wherein the step of placing at least one plate member between an upper spinous process and a lower spinous process of a spine comprises placing a first plate member adjacent to the upper spinous process and placing a second plate member adjacent to the lower spinous process;
    rotating a first scissoring element such that an upper end of the first scissoring element extends beyond an upper surface of the at least one plate member and a lower end of the first scissoring element extends beyond a lower surface of the at least one plate member;
    rotating a second scissoring element such that an upper end of the second scissoring element extends beyond the upper surface of the at least one plate member and a lower end of the second scissoring element extends beyond the lower surface of the at least one plate member; and
    locking the first and second scissoring elements in a fixed position to stabilize the upper and lower spinous processes.

12. The method of claim 11, wherein the step of locking the first and second scissoring elements in a fixed position comprises locking the first and second scissoring elements in a fixed position relative to one another using a fastener.

13. The method of claim 12, wherein the step of locking the first and second scissoring elements in a fixed position comprises tightening the fastener, wherein the fastener extends through the first scissoring element and the second scissoring element.

14. The method of claim 11, wherein the second plate member is positioned substantially parallel to the first plate member.

15. The method of claim 11, wherein the step of rotating a first scissoring element comprises:
   rotating the first scissoring element such that an inner surface of an upper end of the first scissoring element rotates into contact with an outer lateral surface of the upper spinous process and an inner surface of a lower end of the first scissoring element rotates into contact with an outer lateral surface of the lower spinous process, and wherein the step of rotating a second scissoring element comprises:
   rotating the second scissoring element such that an inner surface of an upper end of the second scissoring element rotates into contact with an outer lateral surface of the upper spinous process opposite from the upper end of the first scissoring element and an inner surface of a lower end of the second scissoring element rotates into contact with an outer lateral surface of the lower spinous process opposite from the lower end of the first scissoring element.

16. The method of claim 11, further comprising using a retractor to spread the upper and lower spinous processes apart to receive the at least one plate member.

17. The method of claim 11, wherein the inner surfaces of the upper ends of the first and second scissoring elements are configured to substantially conform to the outer lateral surfaces of the upper spinous process and the inner surfaces of the lower ends of the first and second scissoring elements are configured to substantially conform to the outer lateral surfaces of the lower spinous process.

* * * * *